(12) United States Patent
Pathak et al.

(10) Patent No.: US 6,322,593 B1
(45) Date of Patent: Nov. 27, 2001

(54) METHOD FOR TREATING CROSS-LINKED BIOLOGICAL TISSUES

(75) Inventors: Chandrashekhar P. Pathak; Mark A. Moore, both of Austin; Richard E. Philips, Jr., San Marcos, all of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/289,262

(22) Filed: Apr. 9, 1999

(51) Int. Cl.[7] .................................................. A61F 2/36
(52) U.S. Cl. ..................................... 623/23.72; 623/11.11
(58) Field of Search ............................. 427/2.1; 568/488; 564/414, 488; 525/50

(56) References Cited

U.S. PATENT DOCUMENTS

| 4,837,017 | 6/1989 | LeVeen et al. ........................ 424/88 |
| 5,188,834 | 2/1993 | Grimm et al. ....................... 424/422 |

*Primary Examiner*—Corrine McDermott
*Assistant Examiner*—Thomas Barrett
(74) *Attorney, Agent, or Firm*—Blossom F. Loo; Timothy L. Scott; Philip S. Lyren

(57) ABSTRACT

A method for treating biological tissue is provided in which a cross-linked biological tissue containing free aldehyde groups is reacted with a suitable neutralization agent in order to chemically block the aldehyde groups from reactivity toward cellular proteins. Also provided is the cross-linked biological tissue so produced which is substantially free of reactive aldehyde groups and, as a result, exhibits reduced toxicity and improved biocompatibility.

32 Claims, No Drawings

METHOD FOR TREATING CROSS-LINKED BIOLOGICAL TISSUES

BACKGROUND OF THE INVENTION

1. Field of the Invention

The present invention relates generally to the field of medical devices for implantation into humans. More particularly, it concerns methods for processing biological tissues for use as bioprosthetic devices.

2. Description of the Related Art

Bioprostheses are devices derived from processed biological tissues to be used for implantation into humans. The development of such devices originated as an attempt to circumvent some of the clinical complications associated with the early development of the mechanical heart valve, and has since resulted in a rapid proliferation of bioprosthetic devices for a variety of applications. Examples of some of the bioprostheses currently used or under development include heart valves, vascular grafts, biohybrid vascular grafts, ligament substitutes pericardial patches, and others.

The primary component of the biological tissues used to fabricate bioprostheses is collagen, a generic term for a family of related extracellular proteins. Collagen molecules consists of three chains of poly(amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine ($NH_2$), acid (COOH) and hydroxyl (OH) groups, in addition to the amide bonds of the polymer backbone, all of which are sites for potential chemical reaction on these molecules.

Because collagenous tissues degrade very rapidly upon implantation into a host recipient, it is necessary to stabilize the tissue if it is to be used clinically. Chemical stabilization by tissue cross-linking, also referred to as tissue fixation, has been achieved using bifunctional and polyfunctional molecules having reactive groups capable of forming irreversible and stable intramolecular and intermolecular chemical bonds with the reactive amino acid side groups present on the collagen molecules.

Molecules having two or more reactive aldehyde groups, also referred to herein as polyfunctional aldehydes, represent the most commonly used class of agents for cross-linking biological tissues. The most widely used of these polyfunctional aldehydes is the five carbon molecule, glutaraldehyde, which has an aldehyde at each end of a linear aliphatic chain. The aldehyde groups of glutaraldehyde and other like molecules can react under physiological conditions with the primary amine groups of collagen molecules to produce the desired cross-linked tissue.

Despite its widespread use, there are a number of drawbacks associated with tissue cross-linking with polyfunctional aldehydes. For example, under typical storage conditions, these compounds are generally self-reactive and will rapidly reach an equilibrium in which numerous polymeric and other species are present (see, for example, Khor (1997) and references cited therein). As a result, a pure solution of a monomeric polyfunctional aldehyde will become highly heterogeneous over time. Indeed, it is these heterogeneous solutions that have been conventionally used in the art for cross-linking biological tissues. Unfortunately, the properties of tissues cross-linked with these solutions may suffer as a result of this heterogeneity, as further described below.

An important issue when using polyfunctional aldehydes for treating biological tissues relates to the toxicity of the resulting cross-linked material. This toxicity is not completely understood, but may result from more than one mechanism. For example, the polymeric products of glutaraldehyde that are present in a heterogeneous glutaraldehyde solution can depolymize in vivo, causing the release of toxic monomeric glutaraldehyde into the recipient of the bioprosthesis. Such leaching of glutaraldehyde can prevent the cellular growth on the bioprosthesis following implantation that is necessary for long term biocompatibility. In addition, because of the presence of polymeric species of glutaraldehyde, there is an undesirable abundance of free aldehyde groups present within the cross-linked tissue. These free, unreacted aldehyde groups are also believed to contribute to the toxicity of aldehyde cross-linked tissues, for example, by reacting with cellular proteins present on the endothelial cells that must proliferate on and around the tissue after implantation.

Another significant drawback associated with polyfunctional aldehyde cross-linking is the propensity of the treated tissues to undergo calcification. For instance, calcification appears to represent the predominant cause of failure of glutaraldehyde-fixed devices (Golomb et al., 1987; Levy et al., 1986; Thubrikar et al., 1983; Girardot et al., 1995). It is believed that the presence of polymeric forms of glutaraldehyde in the cross-linked tissue may contribute to such calcification, possibly by serving as a physical point of calcification (Thoma et al., 1987).

Thus, it is a significant disadvantage that free aldehyde groups are present in tissue that has been cross-linked with heterogeneous polyfunctional aldehyde solutions. The present invention is directed to overcoming or at least reducing the effects of one or more of the problems set forth above. In particular, a method has been developed greatly reduces the toxicity and increases the biocompatibility of tissues that have been cross-linked with polyfunctional aldehydes.

SUMMARY OF THE INVENTION

There is a need within the field of bioprosthetics for simple, cost-effective methods for cross-linking biological tissues which overcome some of the limitations associated with aldehyde cross-linking and which provide bioprosthetic devices with desirable mechanical characteristics and a reduced susceptibility to calcification, while minimizing the potential for toxicity. This invention broadly concerns methods for cross-linking biological tissues, and the cross-linked tissue so produced, by employing a chemical approach for neutralizing the free, unreacted aldehyde groups present in an aldehyde cross-linked tissue.

Therefore, according to one aspect of the present invention, the free aldehyde groups present in a cross-linked tissue may be neutralized by reaction with an appropriate neutralizing agent/compound. The neutralizing agent will contain a chemical group or functionality that can be reacted with free aldehyde groups within a cross-linked tissue to produce a product having reduced cellular toxicity compared to the aldehyde groups with which the neutralizing agent is reacted. Consequently, a cross-linked tissue treated in accordance with the method of the present invention will have a reduced cellular toxicity relative to the a cross-linked tissue that is not treated by this method.

Suitable neutralizing agents for use in the invention may include any of a wide variety of inorganic salts that are aldehyde-reactive, i.e., are capable of reacting with the free aldehyde groups in a cross-linked tissue. By contacting a cross-linked tissue with a neutralizing agent according to this method, free aldehyde groups present in the cross-linked tissue can be effectively neutralized/stabilized, thereby providing a tissue with reduced toxicity and improved biocompatibility.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

A method is provided by the present invention which employs a chemical neutralization approach for minimizing or eliminating the undesired presence of free aldehyde groups in a cross-linked tissue. Essentially any cross-linked tissue containing free-aldehyde groups is suitable for treatment according to the present invention. Typically, the tissue is one that has been previously cross-linked by a polyfunctional aldehyde, or other aldehyde-containing compound. A "polyfunctional aldehyde," as the term is used herein, refers to a molecule that contains two or more aldehyde functionalities. The other constituents present on the polyfunctional aldehyde are not critical provided they do not adversely effect the ability of the aldehyde groups to be collagen-reactive and thereby capable of producing cross-linked biological tissues. Examples of polyfunctional aldehydes commonly used for producing a cross-linked tissue include those which contain an aliphatic component comprising a linear or branched chain having from 2 to about 36 carbon atoms. Most typically, cross-linking processes employ the use of an aldehyde having from 2 to about 10 carbon atoms, such as the linear five-carbon alkyl di-aldehyde, glutaraldehyde. Of course, other like materials having appropriate aldehyde functionalities are also suitable.

The techniques and conditions for producing cross-linked tissues with aldehyde-containing cross-linking agents are well known and readily available to the skilled individual in the art (for example, see Zilla et al.). In these processes, a tissue is typically contacted with a polyfunctional aldehyde solution for a period of time and under conditions effective to result in the desired degree of cross-linking of collagen and other cellular proteins within the tissue. Procedures for monitoring the progress and/or completion of the cross-linking reaction are also well known. This can be accomplished, for example, by evaluating the shrinkage temperature and/or the quantity of extractable protein present in the treated tissue, as further illustrated below.

Unfortunately, tissues that are cross-linked with polyfunctional aldehydes using conventional approaches contain free aldehyde groups which can adversely compromise their efficacy for use in bioprosthetic devices. Therefore, according to the present invention, in order to minimize or prevent the undesriable consequences of free aldehyde groups present in a cross-linked tissue, the cross-linked tissue is contacted with a neutralizing agent under conditions in which the neutralizing agent reacts with the free aldehyde groups to form a stable, substantially non-reactive product. "Substantially non-reactive" means that the product of the reaction between an aldehyde group and the neutralizing agent has reduced reactivity toward collagen and other cellular proteins compared with the aldehyde group. A neutralized aldehyde group so produced is substantially non-toxic to the host and is non-reactive with cellular and/or extracellular proteins with which it may contact following implantation into a human.

The precise structural characteristics of the neutralizing agent are not critical provided the agent will react with the free aldehyde groups within a cross-linked tissue in a manner which substantially neutralizes the reactivity of the aldehyde groups, and the toxicity associated therewith. Of course, it will generally be desired that the chemical constituents of the neutralized aldehyde groups be sufficiently stable under physiological conditions or other conditions to which the treated material will be exposed. Furthermore, the neutralized aldehyde groups produced according to the invention preferably do not result, either directly or indirectly, in an environment that is substantially toxic or denaturing to the tissue, or that otherwise affects in an adverse manner the structure and/or function of the cross-linked tissue or the tolerance by the host into which the cross-linked tissue is to be implanted.

Suitable neutralizing agents for use in the present invention may be selected from any of a variety of inorganic salts. For example, inorganic salts containing oxygen and sulfur atoms have been found particularly useful in this regard, and may include, but are not limited to, sulfite salts such as sodium bisulfite, potassium bisulfite, lithium bisulfite, sodium metabisulfite, potassium metabisulfite, lithium metabisulfite, sodium hydrosulfite, potassium hydrosulfite, lithium hydrosulfite, hydrogen sulfite, and other like compounds.

The neutralizing agents according to the invention will typically have a high degree of solubility in aqueous solutions and will readily penetrate the tissue being treated. The concentration of the neutralizing agent or agents in the solution with which the cross-linked tissue is contacted may vary considerably while still achieving the same end result. This concentration will typically be in the range of about 0.1 wt. % to about 10 wt. %, more typically between about 1 wt % and about 5 wt. %.

The conditions under which the neutralizing reaction is performed are not critical provided they are compatible with the desired reaction for substantially neutralizing the free aldehydes present in the cross-linked tissue. As will be apparent to the skilled individual, these conditions may vary depending upon the nature of the sample being treated and the particular neutralizing agent or agents being used. In most instances, the reactions will occur with acceptable kinetics by simply contacting the cross-linked tissue with the neutralizing agent in a physiological environment, e.g., an aqueous solution having a pH between about 5 and 9, preferably between about 6 and 8. The pH range most optimal for the neutralization reaction may vary depending on the specifics of the application, but can be readily determined by the skilled individual in the art. Of course, in some situations, routine experimental optimization may be necessary and/or preferred in order to arrive at the conditions most desired for a particular application.

The length of the neutralizing reaction is not critical so long as the tissue and the neutralizing agent remain in contact for a length of time sufficient to allow the reaction to progress to the desired extent, generally until substantially all of the free aldehyde groups within the tissue have be neutralized. Time of treatment may vary depending on the type of tissue being treated, the particular neutralizing agent used, and its concentration in the solution with which the tissue is contacted. However, the time of treatment should not be so long as to adversely effect the tissue to an undesirable extent. The tissue is generally contacted with the neutralizing agent solution for a period from about one minute to one day or more. More typically, the reaction time will range from about one minute to about 12 hours.

Neutralization reaction temperatures, pressures, etc., are not critical and will typically be selected as a matter of operational convenience for a given application. Of course, such conditions are preferably selected so as to not adversely compromise the progression of the neutralization reaction or the integrity of the tissue being treated. Identification of optimal temperature, pressure, and other reaction conditions for a particular agent and/or application will not generally be necessary, but can be readily evaluated, if desired, without undue experimentation. Generally, the cross-linking reaction can be carried out at any desired temperature provided it does not substantially exceed the tissue denaturation temperature of about 62 deg. C. Thus, suitable reaction temperatures for use in this invention may range from about 0 deg. C. to about 60 deg. C., preferably from about 20 deg. C. to about 50 deg. C.

After the neutralization reaction has proceeded for a time and under conditions effective to provide a substantially neutralized product, the sample is generally washed several times prior to implantation. This can be carried out, for example, with water, alcohol, or any of a variety of other suitable solutions.

Various types of biological tissues derived from numerous animal sources and parts of the anatomy can be treated in accordance with this invention. Thus, the tissue can be derived from sources including, but not limited to, human, bovine, porcine, equine, sheep, kangaroo, rabbit etc., and may comprise tendons, ligaments, heart valves, tissues to construct heart valves such as dura matter and pericardium, vascular grafts, biohybrid vascular grafts, patches, and other like materials. For some applications, it may be desired to manipulate the tissue in some manner so as to provide it in a particular form/shape, for example using metallic stents, prior to the cross-linking and/or neutralization reactions. In this way, the tissue may be treated in the particular three-dimensional geometric configuration of the bioprosthesis to be implanted.

The following examples are provided to demonstrate certain illustrative embodiments of this invention. It should be appreciated by those skilled in the art that the techniques disclosed in the examples which follow represent those found by the inventors to function in the practice of the invention and thus can be considered to constitute examples of illustrative modes for its practice. However, those skilled in the art should, in light of the present disclosure, appreciate that many changes can be made in the specific embodiments which are disclosed and still obtain a like or similar result without departing from the spirit and scope of the invention.

EXAMPLE 1

Tissue fixation/cross-linking of bovine pericardium tissue (~1 cm×1 cm samples) was carried out at room temperature in a solution of 0.25% glutaraldehyde (Aldrich Chemical) in phosphate buffered saline at pH 7.2 (PBS) for either 5 or 16 hours. After the treatment, the tissues samples were washed with PBS (50 ml×3) and either used immediately for cytotoxicity assays or stored in 50% ethanol until further use.

Bovine pericardium samples cross-linked in 0.25% glutaraldehyde for 5 hours were treated at various sodium bisulfite solution concentrations and for various lengths of time. After the treatments, samples were washed with PBS (30ml×3) and used immediately for cytotoxicity experiment. Other samples were washed with PBS and stored in 50% ethanol.

Cytotoxicity assays were performed using BALB-3T3 cells (American Type Tissue Collection, Rockville, Md.). The cells were maintained in DMEM media (Gibco BRL) containing 50 U/ml penicillin, 50 ug/ml streptomycin, 1 mM sodium pyruvate, 1.5 g/L Sodium bicarbonate, 0.1 mM non-essential amino acids (Gibco-BRL), and 10% Calf Serum (hyClone). 50,000 cells/well were seeded in a 24 well polystyrene microtiter tissue culture dish. To evaluate cytotoxicity, tissue samples were placed into 2.2 ml of media and incubated at 37° C. with 5% $CO_2$. After 24 hours, 1 ml of media was placed into the well and the cells were incubated for another 24 hours. An MTT (3-(4,5-dimethylithiazol-2yl)-2,5-diphenyl tetrazolium bromide) in-vitro toxicology assay (Sigma Chemical) was performed according to the instructions provided by manufacturer. The MTT assay uses mithochondrial dehydrogenase activity as a measure of cellular viability. The results of MTT assay are reported as % viability of cells as compared to control/untreated cells.

The results of the above described experiments are summarized in Table 1 below.

TABLE 1

| Glutaraldehyde Treatment | Bisulfite Treatment | Microscope observations | % Viability |
|---|---|---|---|
| 0.25% in PBS, 5 h | None | Round cells with no attachment | 20 |
| 0.25% in PBS, 5 h | 1%, 1 h | Monolayer cells with normal morphology | 103 |
| 0.25% in PBS, 16 h | None | Round cells with no attachment to surface | 7 |
| 0.25% in PBS, 16 h | 0.2%, 6 h | Monolayer cells with normal morphology | 28 |
| 0.25% in PBS, 16 h | 2%, 10 min. | Monolayer cells with normal morphology | 30 |
| 0.25% in PBS, 16 h | 2%, 6 h | Monolayer cells with normal morphology | 52 |
| 0.25% in PBS, 16 h | 2%, 24 h | Monolayer cells with normal morphology | 80 |

From Table 1, it is clear that the viability of BALB-3T3 cell is severely comprised by tissue samples treated with glutaraldehyde for either 5 hours or 16 hours (viability=20% and 7%, respectively). However, if the glutaraldehyde cross-linked samples are treated with sodium bisulfite prior to incubation with the cells, viability is greatly improved. Thus, sodium bisulfite treatment effectively reduces the toxicity associated with glutaraldehyde cross-linked tissues.

EXAMPLE 2

Cross-linking biological tissue results in less extractable protein within the material. Protein extraction assays were performed by extracting 10–20 mg of tissue with 10–20 ul of an extraction solution containing 50 mM Tris-HCl, 10% glycerol, 4% mercaptoethanol, 1% sodium dodecyl sulfate, 0.5M NaCl and 0.01% bromophenol blue. The extracted solution was then analyzed on a 4–20% acrylamide:bisacrylamide (37.5:1) Mini-PROTEAN II ready Gel (Biorad Inc).

The shrinkage temperatures of the treated tissues were also determined using standard differential scanning calorimetric analysis. Typically, 2–10 mg of tissue was heated at the rate of 10 deg. C. per minute under nitrogen atmosphere. The onset of the endotherm observed at about 60–80 deg. C. was used as the shrinkage temperature. An increase in the shrinkage temperature is an indication that cross-linking has occurred.

The results obtained from these experiments are summarized below in Table 2:

TABLE 2

| Glutaraldehyde Treatment | Bisulfite Treatment | Extractable Protein | Shrink Temperature |
|---|---|---|---|
| 0.25% in PBS, 16h | None | NO | 84.6 |
| 0.25% in PBS, 16h | 2%, 6h | NO | 79.2 |
| 0.25% in PBS, 16h | 2%, 24h | NO | 76.6 |
| None (unfixed tissue) | None | YES | 66.3 |

From Table 2, it is apparent that there are no extractable proteins present following sodium bisulfite treatment of glutaraldehyde cross-linked tissue, indicating that this treatment has not adversely comprised the integrity of the tissue. The shrinkage temperatures of the sodium bisulfite treated samples were somewhat reduced compared with untreated controls, however they remained significantly higher that for unfixed tissue.

The particular embodiments disclosed above are illustrative only, as the invention may be modified and practiced in different but equivalent manners apparent to those skilled in the art having the benefit of the teachings herein. More specifically, it will be apparent that certain agents which are chemically and/or physiologically related may be substituted for the agents described herein while the same or similar results would be achieved. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

REFERENCES

The following references, to the extent that they provide exemplary procedural or other details supplementary to those set forth herein, are specifically incorporated herein by reference.

Girardot et al., J Biomed Mater Res (1995) 29: 793–801
Golomb et al., Am J Pathol (1987) 127: 122–130
Khor, Biomaterials (1997) 18: 95–105
Levy et al., In: Williams D F, ed. CRC Critical Rev. in Biocompatibility, Vol. 2 (1986): 147–187
Thoma et al., J Biomat. App. (1987) 1: 449
Thubrikar et al., J Thorac Cardiovasc Surg (1983) 86: 115–125
Zilla et al., J Heart Valve Dis (1997) 6: 492–501

What is claimed:

1. A method for treating a biological tissue which comprises contacting a cross-linked biological tissue which contains a plurality of free aldehyde groups with an inorganic salt solution comprising one or more sulfite salts under conditions in which said inorganic salt solution reacts with said free aldehyde groups to form a substantially non-reactive product.

2. The method of claim 1, wherein the inorganic salt solution comprises an inorganic salt selected from the group consisting of sodium bisulfite, potassium bisulfite, lithium bisulfite, sodium metabisulfite, potassium metabisulfite, lithium metabisulfite, sodium hydrosulfite, potassium hydrosulfite, lithium hydrosulfite and hydrogen sulfite.

3. The method of claim 1, wherein the cross-linked tissue is contacted with the inorganic salt solution, wherein the inorganic salt solution has an inorganic salt concentration of about 0.1 wt. % to about 10 wt. %.

4. The method of claim 1, wherein the cross-linked tissue is contacted with the inorganic salt solution, wherein the inorganic salt solution has an inorganic salt concentration of about 1 wt. % to about 5 wt. %.

5. The method of claim 1, wherein the cross-linked tissue is contacted with the inorganic salt solution for a period of time from about one minute to about 24 hours.

6. The method of claim 1, wherein the cross-linked tissue which contains a plurality of free aldehyde groups is a tissue that is cross-linked with a polyfunctional aldehyde.

7. The method of claim 6, wherein the polyfunctional aldehyde is an aliphatic compound having 2–36 carbon atoms.

8. The method of claim 6, wherein the polyfunctional aldehyde is an aliphatic compound having 2–10 carbon atoms.

9. The method of claim 6, wherein the polyfunctional aldehyde is glutaraldehyde.

10. The method of claim 1, wherein the cross-linked biological tissue is a prosthetic heart valve, vascular graft, tendon, ligament, or patch.

11. Cross-linked biological tissue produced according to the method of claim 1.

12. A method for treating biological tissue which comprises contacting a tissue that is cross-linked with a polyfunctional aldehyde and which contains a plurality of free aldehyde groups with an inorganic salt solution comprising one or more sulfite salts under conditions in which said inorganic salt reacts with said free aldehyde groups to form a substantially non-reactive product.

13. The method of claim 12, wherein the inorganic salt solution comprises one or more sulfite salts selected from the group consisting of sodium bisulfite, potassium bisulfite, lithium bisulfite, sodium metabisulfite, potassium metabisulfite, lithium metabisulfite, sodium hydrosulfite, potassium hydrosulfite, lithium hydrosulfite and hydrogen sulfite.

14. The method of claim 12, wherein the concentration of the inorganic salt in the inorganic salt solution is about 0.1 wt. % to about 10 wt. %.

15. The method of claim 12, wherein the concentration of the inorganic salt in the inorganic salt solution is about 1 wt. % to about 5 wt. %.

16. The method of claim 12, wherein the cross-linked tissue is contacted with the inorganic salt solution for a period of time from about one minute to about 24 hours.

17. The method of claim 12, wherein the cross-linked tissue which contains a plurality of free aldehyde groups is a tissue that is cross-linked with a polyfunctional aldehyde.

18. The method of claim 17, wherein the polyfunctional aldehyde is an aliphatic compound having 2–36 carbon atoms.

19. The method of claim 17, wherein the polyfunctional aldehyde is an aliphatic compound having 2–10 carbon atoms.

20. The method of claim 17, wherein the polyfunctional aldehyde is glutaraldehyde.

21. The method of claim 12, wherein the cross-linked biological tissue is a prosthetic heart valve, vascular graft, tendon, ligament, or patch.

22. Cross-linked biological tissue produced according to the method of claim 14.

23. A method for treating biological tissue which comprises contacting a tissue that is cross-linked with glutaraldehyde and which contains a plurality of free aldehyde groups with sodium bisulfite, potassium bisulfite or lithium bisulfite solution under conditions in which said sodium bisulfite, potassium bisulfite or lithium bisulfite reacts with said free aldehyde groups to form a substantially non-reactive product.

24. The method of claim 23, wherein the sodium bisulfite, potassium bisulfite or lithium bisulfite salt solution has a sodium bisulfite, potassium bisulfite or lithium bisulfite concentration of about 0.1 wt. % to about 10 wt. %.

25. The method of claim 23, wherein the sodium bisulfite, potassium bisulfite or lithium bisulfite salt solution has a sodium bisulfite, potassium bisulfite or lithium bisulfite concentration of about 1 wt. % to about 5 wt. %.

26. The method of claim 23, wherein the cross-linked tissue is contacted with the sodium bisulfite, potassium bisulfite or lithium bisulfite salt solution for a period of time from about one minute to about 24 hours.

27. The method of claim 23, wherein the cross-linked tissue which contains a plurality of free aldehyde groups is a tissue that is cross-linked with a polyfunctional aldehyde.

28. The method of claim 27, wherein the polyfunctional aldehyde is an aliphatic compound having 2–36 carbon atoms.

29. The method of claim 27, wherein the polyfunctional aldehyde is an aliphatic compound having 2–10 carbon atoms.

30. The method of claim 27, wherein the polyfunctional aldehyde is glutaraldehyde.

31. The method of claim 23, wherein the cross-linked biological tissue is a prosthetic heart valve, vascular graft, tendon, ligament, or patch.

32. Cross-linked biological tissue produced according to the method of claim 23.

* * * * *